(12) United States Patent
Polymeropoulos et al.

(10) Patent No.: US 12,146,185 B2
(45) Date of Patent: Nov. 19, 2024

(54) GENETIC MARKERS FOR ENHANCING EFFICACY OF ANTIPSYCHOTIC TREATMENT WITH ILOPERIDONE

(71) Applicant: Vanda Pharmaceuticals Inc., Washington, DC (US)

(72) Inventors: Mihael H. Polymeropoulos, Potomac, MD (US); Sandra Smieszek, Cleveland, OH (US)

(73) Assignee: Vanda Pharmaceuticals Inc., Washington, DC (US)

( * ) Notice: Subject to any disclaimer, the term of this patent is extended or adjusted under 35 U.S.C. 154(b) by 281 days.

(21) Appl. No.: 17/536,306

(22) Filed: Nov. 29, 2021

(65) Prior Publication Data

US 2022/0081710 A1 Mar. 17, 2022

Related U.S. Application Data

(63) Continuation of application No. 16/542,575, filed on Aug. 16, 2019, now Pat. No. 11,214,827.

(60) Provisional application No. 62/725,016, filed on Aug. 30, 2018.

(51) Int. Cl.
*C12Q 1/6827* (2018.01)
*G16H 50/30* (2018.01)

(52) U.S. Cl.
CPC ........... *C12Q 1/6827* (2013.01); *G16H 50/30* (2018.01); *C12Q 2600/112* (2013.01); *C12Q 2600/156* (2013.01)

(58) Field of Classification Search
CPC .................. C12Q 2600/106; C12Q 1/6827
See application file for complete search history.

(56) References Cited

U.S. PATENT DOCUMENTS

| | | | |
|---|---|---|---|
| 8,460,867 B2 | 6/2013 | Kudaravalli et al. |
| 8,586,610 B2 | 11/2013 | Wolfgang et al. |
| 9,080,214 B2 | 7/2015 | Lavedan et al. |
| 9,138,432 B2 | 9/2015 | Wolfgang et al. |
| 9,328,387 B2 | 5/2016 | Lavedan et al. |
| 9,458,507 B1 | 10/2016 | Lavedan et al. |
| 10,272,076 B2 | 4/2019 | Wolfgang et al. |
| 10,441,580 B2 | 10/2019 | Polymeropoulos et al. |
| 10,874,659 B2 | 12/2020 | Phadke et al. |
| 10,987,346 B2 | 4/2021 | Polymeropoulos et al. |
| 11,214,827 B2 | 1/2022 | Polymeropoulos et al. |
| 2008/0027106 A1 | 1/2008 | Kudaravalli et al. |
| 2010/0144781 A1 | 6/2010 | Fu et al. |
| 2010/0249188 A1 | 9/2010 | Lavedan et al. |
| 2010/0292211 A1 | 11/2010 | Lavedan et al. |
| 2011/0021566 A1 | 1/2011 | Lavedan et al. |
| 2012/0053207 A1 | 3/2012 | Lavedan et al. |
| 2014/0039008 A1 | 2/2014 | Wolfgang et al. |
| 2016/0122821 A1 | 5/2016 | Liu et al. |
| 2019/0015415 A1 | 1/2019 | Konsoula et al. |

OTHER PUBLICATIONS

Medline Plus. Retrieved on May 14, 2024 from the internet: medlineplus.gov/druginfo/meds/a609026.html. (Year: 2024).*
Drugbank. Retrieved on May 14, 2024 from the internet: go.drugbank.com/drugs/DB04946. (Year: 2024).*
NAMI. Retrieved on May 14, 2024 from the internet: www.nami.org/about-mental-illness/treatments/mental-health-medications/types-of-medication/iloperidone-fanapt/. (Year: 2024).*
Tonin et al. Core Evidence. 2016. 11:49-61. (Year: 2016).*
WebMD. Retrieved on May 14, 2024 from the internet: www.webmd.com/drugs/2/drug-153411/iloperidone-oral/details. (Year: 2024).*
Albers et al., "Iloperidone: a new benzisoxazole atypical antipsychotic drug. Is it novel enough to impact the crowded atypical antipsychotic market?" Expert Opin. Investig. Drugs, 17:61-75, 2008, 15 pages.
Lavedan et al., "Association of the NPAS3 gene and five other loci with response to the antipsychotic iloperidone identified in a whole genome association study," Molecular Psychiatry, 14:804-19, 2009, 16 pages.
Tonin et al., "Iloperidone in the treatment of schizophrenia: an evidence-based review of its place in therapy," Core Evidence, 11:49-61, 2016, 13 pages.
Volpi et al., "Applicability of a Genetic Signature for Enhanced Iloperidone Efficacy in the Treatment of Schizophrenia," J. of Clinical Psychiatry, 70:801-09, Abstract Only, 2009, 1 page.

* cited by examiner

*Primary Examiner* — Joseph G. Dauner
(74) *Attorney, Agent, or Firm* — Hoffman Warnick LLC

(57) ABSTRACT

The present invention relates to the selection of patients with enhanced antipsychotic treatment efficacy with iloperidone based on a patient's genotype at one or more single nucleotide polymorphism (SNP) loci and to treatment of such patients based upon the identification of their genetic information.

13 Claims, 4 Drawing Sheets

GENETIC MARKERS FOR ENHANCING EFFICACY OF ANTIPSYCHOTIC TREATMENT WITH ILOPERIDONE

CROSS REFERENCE TO RELATED APPLICATIONS

The present application is a continuation of co-pending U.S. patent application Ser. No. 16/542,575, filed Aug. 16, 2019, which claims the benefit of U.S. Provisional Application No. 62/725,016, filed Aug. 30, 2018. The entirety of each of the foregoing is incorporated by reference as though fully set forth herein.

BACKGROUND OF THE INVENTION

The invention relates generally to improvements in the treatment of psychotic symptoms, and more particularly, to enhancing the effectiveness of the use of iloperidone, an iloperidone metabolite, or pharmaceutically-acceptable salts thereof in treating an individual's psychotic symptoms, based on the individual's genotype at one or more single nucleotide polymorphism (SNP) loci.

Schizophrenia is a psychotic disorder affecting approximately 1% of the US population. It is characterized by the presence of positive symptoms (e.g., hallucinations and delusions) and negative symptoms (e.g., blunted affect and social withdrawal), as well as impairment of cognitive functions (e.g., verbal memory, information processing). There is much evidence that schizophrenia may not be caused by a single major gene, but rather by several interacting susceptibility loci.

The nature and severity of an individual's schizophrenia may be measured using a number of scales, the most widely used being the Positive and Negative Syndrome Scale (PANSS). A number of PANSS subscales may also be used, such as the PANSS general psychopathology subscale (PANSS-GP), the PANSS positive symptom subscale (PANSS-P), and the PANSS negative symptom subscale (PANSS-N). The PANSS total score (PANSS-T) is comprised of all PANSS subscales.

A number of drugs have been approved to treat schizophrenia. However, patient response to treatment remains highly variable, and the discontinuation rate with antipsychotic treatment is high. No single antipsychotic agent offers optimal effect for every patient with schizophrenia. Few data are available to guide clinicians and patients in the selection of the most appropriate medication, and in the improvement of treatment specificity for an individual patient.

Iloperidone (1-[4-[3-[4-(6-fluoro-1,2-benzisoxazol-3-yl)-1-piperidinyl]propoxy]-3-methoxyphenyl]ethanone) is an atypical antipsychotic disclosed in U.S. Pat. RE39,198. Metabolites of iloperidone, e.g., P88 (also referred to as P-88-8891 or 1-[4-[3-[4-(6-fluoro-1,2-benzisoxazol-3-yl)-1-piperidinyl]propoxy]-3-methoxyphenyl]ethanol), are also useful in the present invention. See, e.g., International Patent Application Publication No. WO03020707, which is incorporated herein by reference. Other iloperidone metabolites include: 1-[4-[3-[4-(6-fluoro-1,2-benzisoxazol-3-yl)-1-piperidinyl]propoxy]-3-hydroxyphenyl]ethanone; 1-[4-[3-[4-(6-fluoro-1,2-benzisoxazol-3-yl)-1-piperidinyl]propoxy]-3-methoxyphenyl]-2-hydroxyethanone; 4-[3-[4-(6-fluoro-1,2-benzisoxazol-3-yl)-1-piperidinyl]propoxy]-3-hydroxy-α-methylbenzene methanol; 4-[3-[4-(6-fluoro-1,2-benzisoxazol-3-yl)-1-piperidinyl]propoxy]-2-hydroxy-5-methoxy-α-methylbenzenemethanol; 1-[4-[3-[4-(6-fluoro-1,2-benzisoxazol-3-yl)-1-piperidinyl]propoxy]-2-hydroxy-5-methoxyphenyl]ethanone; and 1-[4-[3-[4-(6-fluoro-1,2-benzisoxazol-3-yl)-1-piperidinyl]propoxy]-2,5-dihydroxyphenyl]ethanone. See U.S. Pat. No. 5,364,866, and International Patent Application Publication Nos. WO9309276 and WO9511680.

Previous studies have investigated associations between iloperidone efficacy and polymorphisms in genes and gene regions including CFTR, NPAS3, XKR4, TNR, GRIA4, GFRA2, and NUDT9P1. These associations are described in, e.g., U.S. Pat. Nos. 9,328,387, 9,458,507, and 9,080,214. Additionally, associations between CYP2D6 and KCNQ1 genotypes and changes in QT interval following the administration of iloperidone are described in U.S. Pat. Nos. 8,586,610, 9,138,432, 8,999,638, and 9,157,121. Such findings relating to the efficacy of iloperidone aid in selection of the most optimal drug and dosage regimen for a particular patient. This in turn aids in safe and effective treatment of psychotic symptoms, diseases, and disorders, with less trial and error.

SUMMARY OF THE INVENTION

The present invention relates to methods for enhancing the treatment of an individual with iloperidone, a metabolite of iloperidone, or a pharmaceutically acceptable salt of iloperidone or the metabolite based on the individual's genotype at one or more single nucleotide polymorphism (SNP) loci associated with antipsychotic response, as well as determining whether a schizophrenia patient will have an enhanced likelihood of responding to antipsychotic therapy based on the individual's genotype at one or more such SNP loci. More particularly, the invention relates to improved methods for the treatment of an individual using an atypical antipsychotic and/or the determination of enhanced likelihood for the efficacy of such treatment based on the individual's genotype at one or more SNP loci shown in Table 3.

In a method consisting of administering to a schizophrenia patient an amount of iloperidone, a metabolite of iloperidone, or a pharmaceutically acceptable salt of iloperidone or the metabolite thereof, effective to treat said patient's schizophrenia, the present invention offers an improvement comprising selecting said patient for treatment based upon a determination that said patient's genotype is selected from the group consisting of: rs2299503-AA, rs13222700-TT, rs11763603-CC, rs7049108-GG, rs579298-TT, rs11176436-TT, and rs17109739-CC. With regard to this improvement, the present invention includes a method for treating a schizophrenia patient with iloperidone, comprising identifying the patient's genotype at one or more of rs2299503, rs13222700, rs11763603, rs7049108, rs579298, rs11176436, or rs17109739; and (1) if the patient has a genotype selected from: rs2299503-AA, rs13222700-TT, rs11763603-CC, rs7049108-GG, rs579298-TT, rs11176436-TT, and rs17109739-CC, then internally administering iloperidone to the patient at a dose of greater than or equal to 12 mg/day and up to 24 mg/day, and (2) if the patient has a genotype selected from: rs2299503-nonAA, rs13222700-nonTT, rs11763603-nonCC, rs7049108-nonGG, rs579298-nonTT, rs11176436-nonTT, and rs17109739-nonCC, then internally administering iloperidone to the patient at a dose that is greater than the dose the patient would otherwise receive to treat the patient's schizophrenia if the patient's rs2299503, rs13222700, rs11763603, rs7049108, rs579298, rs11176436, and rs17109739 genotypes were unknown.

With regard to the foregoing method, the invention herein also may be practiced, if the patient has a genotype selected from: rs2299503-nonAA, rs13222700-nonTT, rs11763603-nonCC, rs7049108-nonGG, rs579298-nonTT, rs11176436-nonTT, and rs17109739-nonCC, by providing enhanced side-effect and efficacy monitoring for the patient concurrently with or after the internally administering. Such monitoring may include, e.g., monitoring for changes to the patient's cardiac rhythm, particularly prolongation of the QT interval, occurrence of tardive dyskinesia, orthostatic hypotension, or other side effects, and monitoring of the degree to which the patient's symptoms are controlled by iloperidone. While patients are routinely monitored for such effects, enhanced monitoring may include more frequent and/or more extensive monitoring, including for example performing periodic electrocardiograms to monitor cardiac rhythms. In addition, the identification of the patient's genotype may be undertaken by (1) obtaining or having obtained a biological sample from the patient; and (2) performing or having performed a genotyping assay on the biological sample to determine the patient's genotype at one or more of rs2299503, rs13222700, rs11763603, rs7049108, rs579298, rs11176436, or rs17109739.

Also, the present invention can encompass a method for determining that a schizophrenia patient, whose genotype at one or more SNPs selected from rs2299503, rs13222700, rs11763603, rs7049108, rs579298, rs11176436, or rs17109739 has been identified, has an enhanced likelihood of responding to treatment with iloperidone, comprising identifying said patient as an enhanced likelihood responder (1) if said patient's genotype includes one or more variants selected from: rs2299503-AA, rs13222700-TT, rs11763603-CC, rs7049108-GG, rs579298-TT, rs11176436-TT, rs17109739-CC and (2) only if said patient's genotype does not include the variants: rs2299503-nonAA, rs13222700-nonTT, rs11763603-nonCC, rs7049108-nonGG, rs579298-nonTT, rs11176436-nonTT, and rs17109739-nonCC.

DETAILED DESCRIPTION

Figure 1:
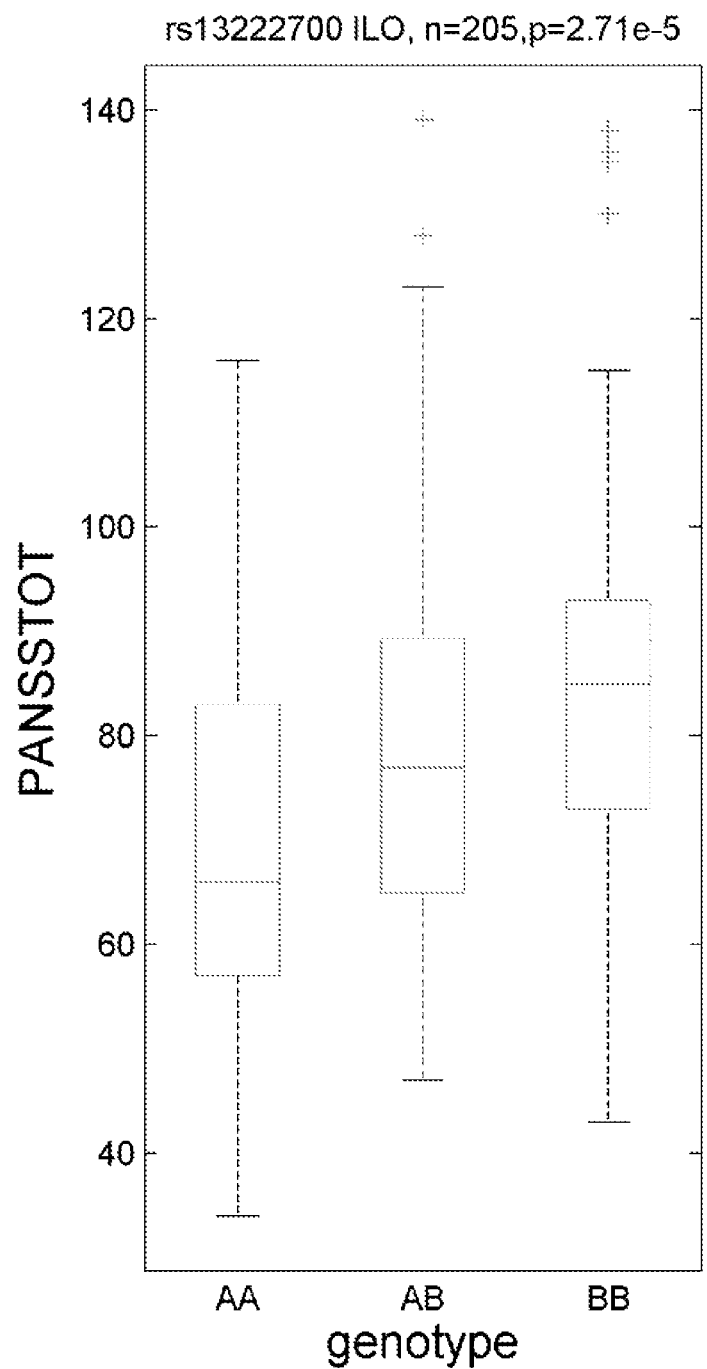
FIG. 1 illustrates iloperidone treatment effect as measured by PANSS-T by genotype.

Various embodiments of the invention provide improved methods for treating psychotic diseases, disorders, and symptoms thereof using iloperidone, an iloperidone metabolite, or a pharmaceutically acceptable salt of iloperidone or the metabolite thereof, selecting patients for such treatment on the basis of identifying those whose gene sequences include genetic variants associated with iloperidone efficacy, and predicting the likelihood that a particular patient will respond significantly and favorably to iloperidone treatment. In various embodiments, the psychotic disease being treated may particularly be schizophrenia.

A method is provided in which iloperidone, a metabolite of iloperidone, or a pharmaceutically acceptable salt of iloperidone is administered to a patient suffering from schizophrenia in an amount effective to treat said patient's schizophrenia, in which the patient is selected on the basis of having a genotype at one or more SNPs that is associated with iloperidone efficacy. The SNPs may include rs2299503, rs13222700, or rs11763603 in GRM8, rs7049108 in NTRK2, rs579298 in SHANK2, rs11176436 in GRIP1, or rs17109739 in NRXN3. In particular, the patient may be selected for treatment on the basis of having a gene sequence that includes one of the following variants: rs2299503-AA, rs13222700-TT, rs11763603-CC, rs7049108-GG, rs579298-TT, rs11176436-TT, or rs17109739-CC, each of which is associated with a significant treatment effect observed in iloperidone-treated schizophrenia patients.

A method is further provided for treating schizophrenia in a patient with iloperidone, including identifying whether the patient's gene sequence includes a variant associated with iloperidone treatment effect. The identifying step may include a number of different methods of identification. In one aspect, identifying a genotype may include performing a genotyping assay on a biological sample collected from the patient to be treated. The biological sample may include, e.g., blood, serum, saliva, urine, et al. as is known in the art. The performance of such an assay may include steps such as, e.g., extracting genomic DNA or mRNA from the biological sample, and sequencing DNA derived from the extracted genomic DNA or from the extracted mRNA, including amplifying a gene region in the extracted genomic DNA or mRNA to prepare a DNA sample enriched with DNA from the relevant gene region. The DNA sample may then be hybridized to nucleic acid probes to determine whether the patient has a genotype of interest.

In some embodiments, identifying a genotype may include reviewing a patient's medical history, result report, or other document containing the result of a previously-performed assay or genetic test. In still further aspects, the identifying may include causing or requesting an assay to be performed by another individual, or causing or requesting the review of the patient's medical history, result report, or other document containing the result of a previously-performed assay or genetic test.

In any event, the method includes identifying the patient's genotype at one or more SNPs associated with iloperidone treatment effect, which may include: rs2299503, rs13222700, rs11763603, rs7049108, rs579298, rs11176436, or rs17109739. If the patient has a genotype selected from the following: rs2299503-AA, rs13222700-TT, rs11763603-CC, rs7049108-GG, rs579298-TT, rs11176436-TT, or rs17109739-CC, then the method includes internally administering iloperidone to the patient at a dose of between 12 mg/day and 24 mg/day, e.g., 12 mg/day, 14 mg/day, 16 mg/day, 18 mg/day, 20 mg/day, 22 mg/day, or 24 mg/day. However, if the patient has a genotype selected from: rs2299503-nonAA, rs13222700-nonTT, rs11763603-nonCC, rs7049108-nonGG, rs579298-nonTT, rs11176436-nonTT, rs17109739-nonCC, the patient may be administered iloperidone at an increased dosage. For example, a patient whose rs2299503, rs13222700, rs11763603, rs7049108, rs579298, rs11176436, and rs17109739 genotypes are unknown, and who has no other known genetic variants associated with poor efficacy of iloperidone or poor metabolism of iloperidone, may be treated using a dosage of, e.g., 18 mg/day to maintain effective control of symptoms of schizophrenia. The same patient, if identified as having a genotype selected from: rs2299503-nonAA, rs13222700-nonTT, rs11763603-nonCC, rs7049108-nonGG, rs579298-nonTT, rs11176436- nonTT, and rs17109739-nonCC, might instead be treated using a dosage of, e.g., 20 mg/day, 22 mg/day, 24 mg/day, or even greater due to the individual's specific genetic variant. Enhanced monitoring of the patient may be indicated at increased doses of iloperidone.

A further method is provided for determining that a patient suffering from schizophrenia has an enhanced likelihood of responding to iloperidone treatment on the basis of a genetic predisposition. Such a method may include identifying the patient's genotype at one or more SNPs selected from rs2299503, rs13222700, rs11763603, rs7049108, rs579298, rs11176436, and rs17109739. As discussed above, the identifying may be accomplished in a number of ways, all of which are contemplated as part of this method. Patients identified as having a genetic variant selected from: rs2299503-AA, rs13222700-TT, rs11763603-CC, rs7049108-GG, rs579298-TT, rs11176436-TT, and rs17109739-CC can be predicted to respond favorably and significantly to schizophrenia treatment with iloperidone. In contrast, patients identified as having a gene sequence including the variants: rs2299503-nonAA, rs13222700-nonTT, rs11763603-nonCC, rs7049108-nonGG, rs579298-nonTT, rs11176436-nonTT, and rs17109739-nonCC are significantly less likely to respond favorably to schizophrenia treatment with iloperidone.

The foregoing methods collectively aid physicians in prospectively identifying patients who will particularly benefit from treatment with iloperidone. The ability to identify patients who are likely to benefit from treatment prior to commencement of treatment itself provides a meaningful benefit to patients and practitioners as it reduces the amount of trial and error that a patient must endure before identifying an effective treatment regimen to gain and maintain control of psychotic symptoms.

An effective amount of iloperidone or an active metabolite thereof may be administered to a subject animal (typically a human but other animals, e.g., farm animals, pets and racing animals, can also be treated) by a number of routes. An effective amount is an amount that during the course of therapy will have a preventive or ameliorative effect on a psychotic disorder, such as schizophrenia, or a symptom thereof, or of bipolar disorder. An effective amount may quantitatively vary depending upon, for example, the patient, the severity of the disorder or symptom being treated, and the route of administration.

It will be understood that the dosing protocol including the amount of iloperidone, a metabolite of iloperidone, or a pharmaceutically acceptable salt of iloperidone or the metabolite thereof actually administered will be determined by a physician in the light of the relevant circumstances including, for example, the condition to be treated, the chosen route of administration, the age, weight, and response of the individual patient, and the severity of the patient's symptoms. Patients should be monitored for possible adverse events.

For therapeutic use, iloperidone, a metabolite of iloperidone, or a pharmaceutically acceptable salt of iloperidone or the metabolite thereof will normally be administered as a pharmaceutical composition as the (or an) essential active ingredient at least one such compound in association with a solid or liquid pharmaceutically acceptable carrier and, optionally, with pharmaceutically acceptable adjuvants and excipients employing standard and conventional techniques.

Pharmaceutical compositions useful in the practice of this invention include suitable dosage forms for oral, parenteral (including subcutaneous, intramuscular, intradermal and intravenous), transdermal, bronchial or nasal administration.

Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. The pharmaceutical compositions may be prepared by conventional techniques appropriate to the desired preparation containing appropriate amounts of iloperidone or an active metabolite thereof. See, for example, Remington's Pharmaceutical Sciences, Mack Publishing Company, Easton, Pa., 17th edition, 1985.

In making pharmaceutical compositions for use in the invention, the active ingredient(s) will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions are preferably formulated in a unit dosage form. The term "unit dosage form" refers to physically discrete units suitable as unitary dosages for human subjects and other mammals, each unit containing a predetermined quantity of active material calculated to produce the desired prophylactic or therapeutic effect over the course of a treatment period, in association with the required pharmaceutical carrier.

Iloperidone and its active metabolites can also be formulated in a controlled release form, e.g., delayed, sustained, or pulsatile release. Various formulations and methods of administering iloperidone and/or its derivatives have been described. For example, U.S. Pat. Nos. 8,227,488; 8,293,765; and 8,614,232 describe an injectable depot formulation comprising iloperidone crystals; and microencapsulated depot formulations of iloperidone and a polyglycolide polylactide glucose star polymer are described in U.S. Pat. Nos. 7,767,230 and 8,815,293.

Example: GRM8, NRXN3, GRIP1, NPAS3, SHANK2, and NTRK2

A genome-wide association study (GWAS) is performed to improve understanding of the pharmacogenomic basis of response to iloperidone treatment of schizophrenia patients. In the GWAS, genotypes of 205 patients are utilized to evaluate treatment with iloperidone. Linear regression is used to directly test the association between single nucleotide polymorphisms (SNPs) and PANSS-T (day 28), correcting for essential covariates including principal components.

The analysis identifies SNPs associated with iloperidone efficacy within the Glutamate Metabotropic Receptor 8 (GRM8), NRXN3, GRIP1, NPAS3, SHANK2, and NTRK2 genes (Tables 1-2). GRM8 is involved in the neurotransmission of glutamate, which plays an important role in the development of schizophrenia and major depressive disorders. The top loci resulting from the association analyses identify a GRM8 variant, rs13222700 ($P<1\times10^{-5}$), located on chromosome 7, with a strong and highly significant signal.

Methods

Patients 18-65 years of age with diagnoses of schizophrenia according to the *Diagnostic and Statistical Manual of Mental Disorders, 4$^{th}$ Edition* are eligible to participate in a randomized, double-blind, placebo- and ziprasidone-controlled, 28-day study of the efficacy and safety of iloperidone. Patients are randomly assigned to iloperidone 12 mg bid, ziprasidone 80 mg bid (active control), or placebo. The primary efficacy variable is change from baseline to the last scheduled observation in PANSS-T using the data from the short-term, double-blind phase. A secondary objective is to identify genetic markers predictive of response to iloperidone. Blood samples are collected, and DNA is extracted from patients who consented to the optional GWAS.

Three analyses of the PANSS-T are conducted: 1) A two-step approach where samples are randomly split into 2 groups of iloperidone-treated patients used to discover SNPs associated with change in PANSS-T (Discovery phase) and a second group to confirm the 100 most significant SNPs (Confirmatory phase). 2) A one-step approach using the Last Observation Carried Forward (LOCF) PANSS-T data of all iloperidone-treated patients. For each SNP, the most parsimonious genetic model (e.g., homozygous for one allele v. all other genotypes [i.e., AA v. AB and BB], heterozygous v. homozygous [i.e., AB v. AA and BB]) was established with respect to iloperidone efficacy using a one-way analysis of variance (ANOVA). 3) A Mixed-effects Model Repeated Measures (MMRM) analysis was subsequently conducted using the best genetic model of each SNP in the MMRM model. MMRM analyses were also conducted with the PANSS subscales PANSS-P, PANSS-N, and PANSS-GP.

The SNPs with a statistically significant association in all 3 analyses of PANSS-T, as well as the best of each analysis are considered significant findings and are listed below in Table 3.

Results

Figure 2:
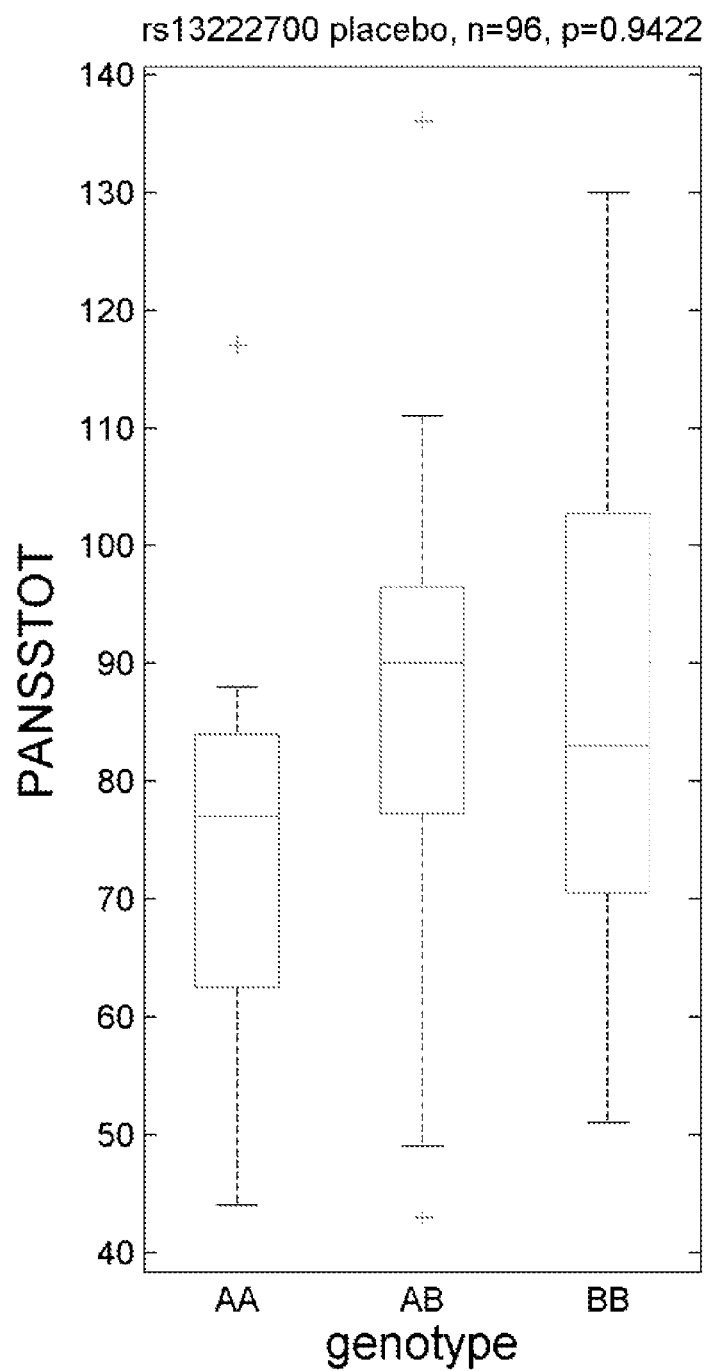
FIG. 2 illustrates placebo treatment effect as measured by PANSS-T by genotype.

In the iloperidone-treated group of schizophrenia patients, the minor allele is associated with lower PANSS-T (FIG. 1). In particular, individuals who are homozygous for the minor allele (i.e. TT rs13222700 genotype) demonstrate significantly higher treatment effect than individuals who are heterozygous (GT rs13222700 genotype) or homozygous for the major allele (i.e. GG rs13222700 genotype). No such association is observed in the placebo group (FIG. 2).

Figure 3:
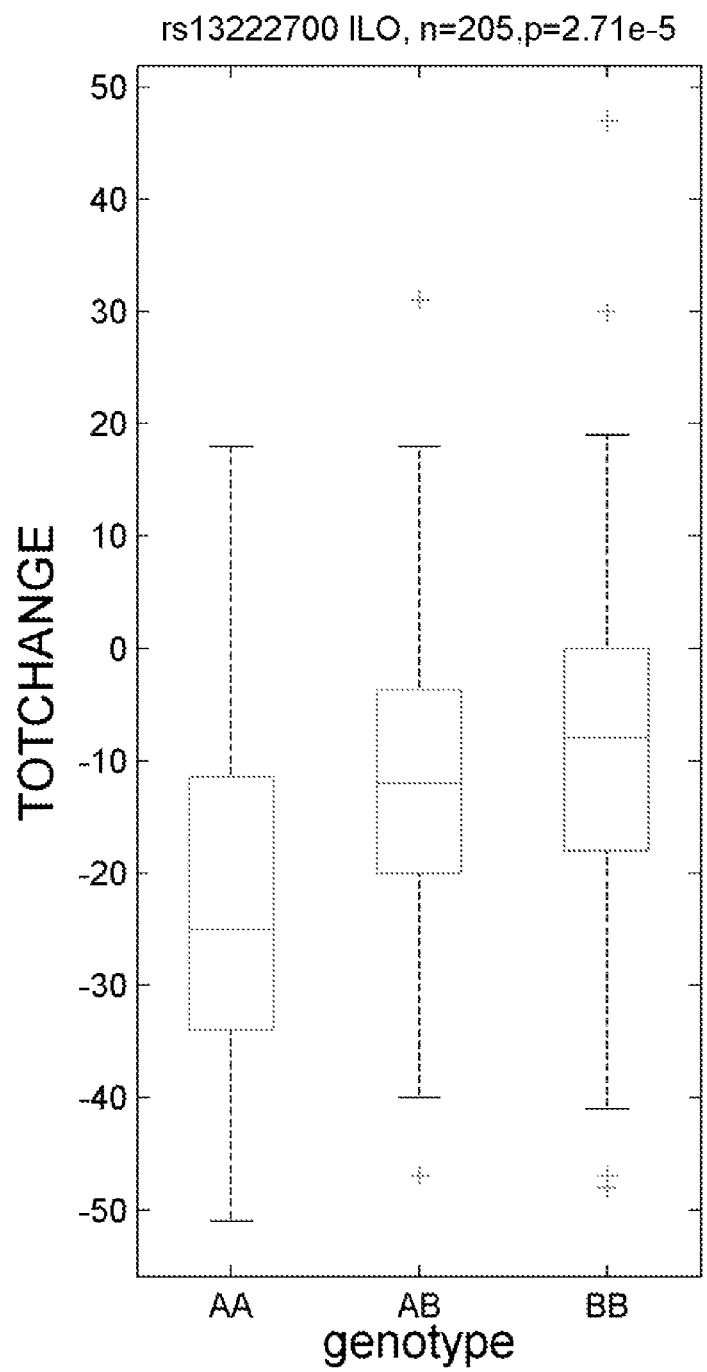
FIG. 3 illustrates iloperidone treatment effect as measured by PANSS-T change by genotype.
Figure 4:
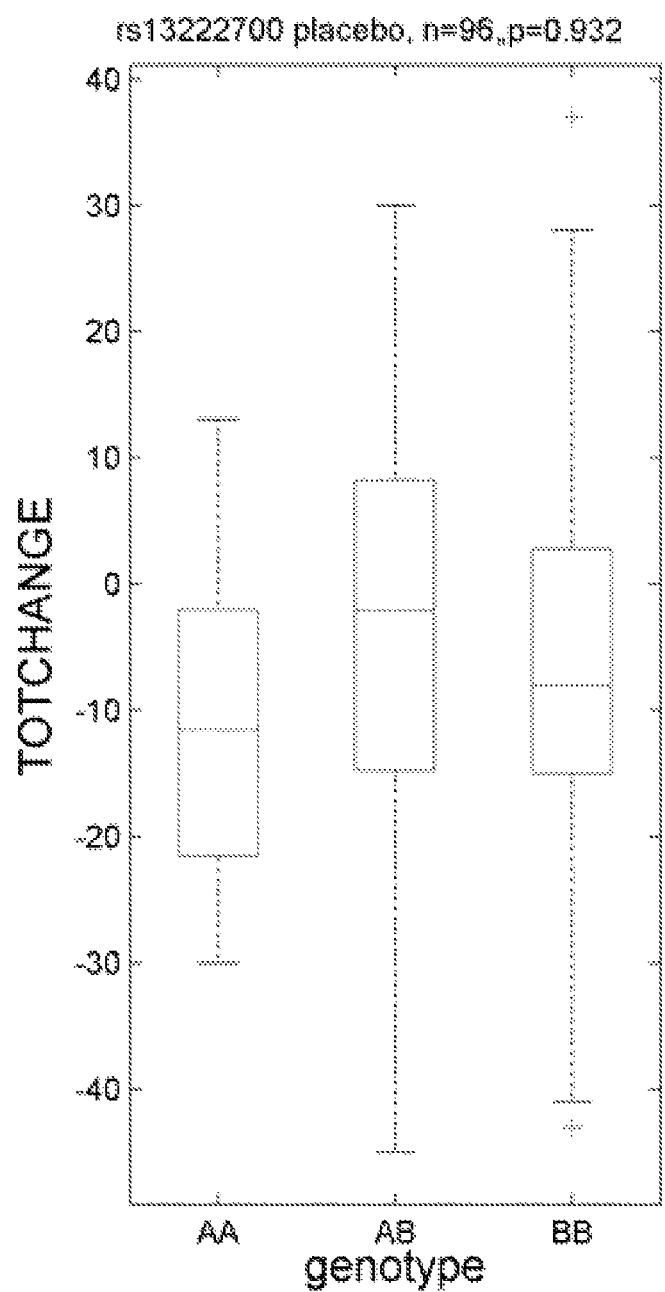
FIG. 4 illustrates placebo treatment effect as measured by PANSS-T change by genotype.

As shown in FIG. 3, using another measure of treatment effect, PANSS-T change, the minor allele is again found to associate with higher treatment effect in the iloperidone-treated group. Individuals who are homozygous for the minor allele (i.e. TT rs13222700 genotype) demonstrate significantly larger change in PANSS-T score following iloperidone treatment than individuals who are heterozygous (GT rs13222700 genotype) or homozygous for the major allele (i.e. GG rs13222700 genotype). No such association is observed in the placebo group (FIG. 4).

A logistic regression is conducted based on binary cutoffs at PANSS-T≥30 and on the top ends of the distribution logistic model, splitting the data set into two groups: robust responders (i.e., responders having PANSS_T change≥30) and weak responders (i.e., responders having PANSS-T change<20). A significant GRM8 signal is observed in allelic tests conducted, that is, linear association is observed with PANSS-T day 28, logistic model with tot change>=30 vs weak (<20) and logistic association with high and low PANSS-T.

Investigation of the regulatory potential shows that rs13222700 is involved in mapping to an enhancer region and may alter the effect of STAT and Sox motifs. Furthermore, analysis of a library of transcription factor binding site position weight matrices predicts that the SNP alters the binding site via 6 transcription factor sites. The locus is a significant (0.00008) eQTL for GRM8. The frequency of the respective rs13222700 genotypes appears below in Table 1.

TABLE 1 rs13222700 genotype frequencies in study groups

|  | Iloperidone | Placebo | Ziprasidone |
|---|---|---|---|
| TT | 24 | 12 | 12 |
| GT | 85 | 37 | 39 |
| GG | 96 | 47 | 44 |
| Minor allele frequency (MAF) | 32.4% | 31.8% | 33.2% |

TABLE 2

Population frequencies of rs13222700

| Population | Allele Count | Allele Number | Number of Homozygotes | Allele Frequency |
|---|---|---|---|---|
| European (Finnish) | 1911 | 3488 | 511 | 0.5479 |
| European (Non-Finnish) | 7285 | 14940 | 1776 | 0.4876 |
| Other | 472 | 980 | 113 | 0.4816 |
| Ashkenazi Jewish | 124 | 302 | 24 | 0.4106 |
| Latino | 321 | 838 | 57 | 0.3831 |
| African | 2087 | 8710 | 262 | 0.2396 |
| East Asian | 102 | 1596 | 2 | 0.06391 |
| South Asian | 0 | 0 | 0 | n/a |
| Total | 12302 | 30854 | 2745 | 0.3987 |

Other SNPs Associated with Iloperidone Response Other top loci associated with iloperidone treatment effect direct us to genes such as NRXN3, GRIP, SHANK2, and NTRK2. Table 3 identifies SNPs found to have a statistically significant association with iloperidone efficacy as measured by PANSS-T.

TABLE 3

SNPs associated with iloperidone treatment effect as measured by PANSS-T

| Locus | SNP RSID | chr | start (hg18) | minor allele | Genotype associated with greater treatment effect | Genotype associated with lower treatment effect | P value |
|---|---|---|---|---|---|---|---|
| GRM8 | rs2299503 | 7 | 126160182 | A | AA | nonAA | 4.94E−05 |
| GRM8 | rs13222700 | 7 | 126167388 | T | TT | nonTT | 2.72E−05 |
| GRM8 | rs11763603 | 7 | 126170541 | C | CC | nonCC | 4.90E−05 |
| NTRK2 | rs7049108 | 9 | 87318257 | A | GG | nonGG | 9.12E−05 |
| SHANK2 | rs579298 | 11 | 70004952 | T | TT | nonTT | 9.32E−06 |
| GRIP1 | rs11176436 | 12 | 65501963 | C | TT | nonTT | 9.08E−05 |
| NRXN3 | rs17109739 | 14 | 79218034 | C | CC | nonCC | 0.000283 |

To leverage the top results, enrichment analysis is conducted which shows enrichment in categories such as regulation of neurotransmitter levels (GO:0001505), regulation of glutamate secretion GO:1903294, impaired synaptic plasticity (P-value: 0.00001), hyperactivity: NTRK2 (p=0.0002), and decreased pre-pulse inhibition (p=0.0009).

These data provide greater understanding of the variability in response to iloperidone treatment in patients with schizophrenia, and support further optimization of the benefit to risk ratio for the affected patients.

The foregoing description of various aspects of the invention has been presented for purposes of illustration and description. It is not intended to be exhaustive or to limit the invention to the precise form disclosed, and modifications and variations are possible. Such modifications and variations that may be apparent to a person skilled in the art are intended to be included within the scope of the invention as defined by the accompanying claims.

What is claimed is:

1. In a method consisting of administering to a patient suffering from bipolar disorder an amount of a compound selected from iloperidone, a metabolite of iloperidone, or a pharmaceutically acceptable salt of iloperidone or the metabolite thereof, effective to treat a symptom of the bipolar disorder, the improvement comprising:
    selecting said patient for treatment based upon a determination that said patient's genotype is selected from the group consisting of : rs2299503-AA, rs13222700-TT, rs11763603-CC, rs7049108-GG, rs579298-TT, rs11176436-TT, and rs17109739-CC.

2. The improvement of claim 1, wherein the compound is selected from iloperidone or the pharmaceutically acceptable salt thereof.

3. The improvement of claim 1, wherein the compound is selected from the metabolite of iloperidone or the pharmaceutically acceptable salt thereof.

4. The improvement of claim 3, wherein the metabolite of iloperidone is P88.

5. A method for treating a patient suffering from bipolar disorder with a compound selected from iloperidone, a pharmaceutically acceptable salt of iloperidone, a metabolite of iloperidone, or a pharmaceutically acceptable salt of the metabolite, comprising:
    identifying the patient's genotype at one or more of rs2299503, or rs13222700, rs11763603, rs7049108, rs579298, rs11176436, or rs17109739; and
    if the patient has a genotype selected from: rs2299503-AA, rs13222700-TT, rs11763603-CC, rs7049108-GG, rs579298-TT, rs11176436-TT, and rs17109739-CC, then internally administering the iloperidone, the metabolite of iloperidone, or the pharmaceutically acceptable salt of the metabolite to the patient at a first dose, and
    if the patient has a genotype selected from: rs2299503-nonAA, rs13222700-nonTT, rs11763603-nonCC, rs7049108-nonGG, rs579298-nonTT, rs11176436-nonTT, and rs17109739-nonCC, then internally administering the iloperidone, the metabolite of iloperidone, or the pharmaceutically acceptable salt of the metabolite to the patient at a second dose that is greater than the first dose.

6. The method according to claim 5, further comprising:
    if the patient has a genotype selected from: rs2299503-nonAA, rs13222700-nonTT, rs11763603-nonCC, rs7049108-nonGG, rs579298-nonTT, rs11176436-nonTT, and rs17109739-nonCC, providing enhanced side-effect and efficacy monitoring for the patient concurrently with or after the internally administering.

7. The method according to claim 5, wherein the step of identifying comprises:
    obtaining or having obtained a biological sample from the patient; and
    performing or having performed a genotyping assay on the biological sample to determine the patient's genotype at one or more of rs2299503, rs13222700, rs11763603, rs7049108, rs579298, rs11176436, or rs17109739.

8. The method of claim 5, wherein the compound is selected from iloperidone or the pharmaceutically acceptable salt thereof.

9. The method of claim 5, wherein the compound is selected from the metabolite of iloperidone or the pharmaceutically acceptable salt thereof.

10. The method of claim 9, wherein the metabolite of iloperidone is P88.

11. The method of claim 5, wherein the first dose is selected from a range of 12 mg/day to 24 mg/day.

12. The method of claim 11, wherein the first dose is 18 mg/day, and the second dose is selected from 20 mg/day, 22 mg/day, and 24 mg/day.

13. The method of claim 5, wherein the second dose is greater than a dose the patient would otherwise be administered if the patient's rs2299503, rs1322270, rs11763603, rs7049108, rs579298, rs11176436, and rs17109739 genotypes were unknown.

* * * * *

UNITED STATES PATENT AND TRADEMARK OFFICE
CERTIFICATE OF CORRECTION

Page 1 of 1

PATENT NO. : 12,146,185 B2
APPLICATION NO. : 17/536306
DATED : November 19, 2024
INVENTOR(S) : Mihael H. Polymeropoulos and Sandra Smieszek It is certified that error appears in the above-identified patent and that said Letters Patent is hereby corrected as shown below:

In the Specification

Column 8, Line 64, delete "GRIP," and insert -- GRIP1, -- therefor.

In the Claims

Column 9, Claim 1, Line 43, delete "consisting of :" and insert -- consisting of: -- therefor.

Column 9, Claim 5, Line 60, delete "or rs13222700," and insert -- rs13222700, -- therefor.

Column 10, Claim 13, Line 60, delete "rs1322270," and insert -- rs13222700, -- therefor.

Signed and Sealed this
Thirty-first Day of December, 2024

Derrick Brent
*Acting Director of the United States Patent and Trademark Office*